(12) United States Patent
Asuka et al.

(10) Patent No.: US 7,125,683 B2
(45) Date of Patent: Oct. 24, 2006

(54) PREPARATIONS FOR DIAGNOSIS EXTRAPANCREATIC SECRETORY FUNCTION

(75) Inventors: Ito Asuka, Tokyo (JP); Tadashi Kohno, Tokyo (JP); Isaburo Hosoi, Tokyo (JP); Junko Hirayama, Tokyo (JP); Kunihiko Shibata, Tokyo (JP); Kenji Maeda, Tokyo (JP)

(73) Assignee: Tokyo Gas Company Limited, Tokyo (JP)

( * ) Notice: Subject to any disclaimer, the term of this patent is extended or adjusted under 35 U.S.C. 154(b) by 120 days.

(21) Appl. No.: 10/362,639

(22) PCT Filed: Aug. 31, 2001

(86) PCT No.: PCT/JP01/07528

§ 371 (c)(1),
(2), (4) Date: Feb. 25, 2003

(87) PCT Pub. No.: WO02/20061

PCT Pub. Date: Mar. 14, 2002

(65) Prior Publication Data

US 2003/0228647 A1    Dec. 11, 2003

(30) Foreign Application Priority Data

Sep. 7, 2000    (JP)    .............................. 2000-272116

(51) Int. Cl.
| C12Q 1/34 | (2006.01) |
| C12Q 1/40 | (2006.01) |
| C12Q 1/37 | (2006.01) |
| A61K 51/02 | (2006.01) |
| A61K 38/46 | (2006.01) |
| A61K 38/47 | (2006.01) |
| A61K 38/48 | (2006.01) |
| A61M 36/04 | (2006.01) |

(52) U.S. Cl. ............................. 435/18; 435/22; 435/23; 424/1.65; 424/1.81; 424/94.6; 424/94.61; 424/94.63

(58) Field of Classification Search .................. 435/19, 435/22, 23, 18; 424/1.65, 1.81, 94.2, 94.6, 424/94.61, 94.63; 549/223
See application file for complete search history.

(56) References Cited

U.S. PATENT DOCUMENTS

| 3,786,140 A * | 1/1974 | Meyer-Bertenrath et al. ......................... 436/172 |
| 3,917,812 A | 11/1975 | Woog et al. |
| 4,279,886 A * | 7/1981 | Allen ........................ 424/1.53 |

(Continued)

FOREIGN PATENT DOCUMENTS

DE    44 26 204 A1 A1    1/1995

(Continued)

OTHER PUBLICATIONS

On-line Medical Dictionary, http://cancerweb.ncl.ac.uk/cgi-bin/omd?query = carrier &action=Search+OMD, defintion of "carrier," Oct. 9, 1997.*

(Continued)

Primary Examiner—Robert A. Wax
Assistant Examiner—Rosanne Kosson
(74) Attorney, Agent, or Firm—Finnegan Henderson Farabow Garrett & Dunner LLP (57) ABSTRACT

A preparation for the diagnosis of pancreatic exocrine function by determining the amount in which a substance administered to a subject or a degradation product or metabolite thereof migrates into the blood and/or is excreted out of the body, wherein the substance is carried by a carrier and released from the carrier when exposed to the action of a pancreatic exocrine function-related factor.

13 Claims, 5 Drawing Sheets

U.S. PATENT DOCUMENTS 4,676,974 A * 6/1987 Hofmann et al. ............. 436/57
5,948,630 A * 9/1999 Singh et al. .................. 435/21

FOREIGN PATENT DOCUMENTS

| EP | 0 966 975 A2 | 12/1999 |
| EP | 989137 A2 * | 3/2000 |
| GB | 2246707 A * | 2/1992 |
| GB | 2 251 381 A | 7/1992 |
| JP | 11 315032 | 11/1999 |
| JP | 2000053697 A * | 2/2000 |

OTHER PUBLICATIONS

D. Rating et al., "Breath Tests: Concepts, Applications And Limitations", *Eur J Pediatr*; 156 (Supp. 1); pp. S18-S23, 1997.
Supplementary European Search Report dated Oct. 25. 2005.
International Search Report dated Nov. 27, 2001.

* cited by examiner

PREPARATIONS FOR DIAGNOSIS EXTRAPANCREATIC SECRETORY FUNCTION

This application is the U.S. national phase of POT Application No. PCT/JP01/07528, filed on Aug. 31, 2001, which claims priority to Japanese Application No. 2000-272116, filed on Sep. 7, 2000.

FIELD OF THE INVENTION

The present invention relates to preparations for the diagnosis of pancreatic exocrine function, drug delivery systems for a medical agent and enteric preparations.

BACKGROUND OF THE INVENTION

"Pancreatic exocrine function tests" are useful for the diagnosis of pancreatic diseases such as chronic and acute pancreatitis and pancreatic cancer. They are also useful for the ascertainment of the condition of a disease, the management of medication and the assessment of the prognosis of a disease in a patient. (As for the general review, see Arvanitakis and Cooke, Gastroenterology, 74:932 (1978); Niederau and Grendell, Gastroenterology, 88:1973 (1985); Goldberg, Bull. Mol. Biol. Med., 15:1 (1990); Lankisch, Int. J. Pancreatology, 14:9 (1993); Bank and Chow, Gastroenterologist, 2:224 (1994); and Steer et al., New Eng. J. Med., 332:1482 (1995).

The standard method for pancreatic exocrine function tests is one which involves inserting a tube through the mouth to the duodenum to collect the duodenal juice. At present, the secretin test is commonly used wherein secretin is intravenously administered to stimulate the secretion of the pancreatic juice prior to the collection. This method is highly accurate since the amounts and components of the pancreatic juice are directly analyzed. However, this method can not be used repeatedly or used for screening because of the very strong stress caused on the patients. It is only available in a relatively small number of medical facilities staffed with highly skilled physicians. Further, since this method requires fluoroscopic tube placement during the collection of the duodenal juice, there is a problem of X ray exposure.

Hence, in repeated or screening tests, simpler methods have been used which require no intubation. At present, the following four methods are mainly used:

1. PFD test wherein a synthetic substrate BT-PABA (N-benzoyl-L-tyrosyl-p-aminobenzoic acid) for chymotrypsin secreted from the pancreas is orally administered and the urinary excretion of PABA (p-aminobenzoic acid), the product of degradation by chymotrypsin, is determined;

2. PLT test wherein a synthetic substrate FDL (fluorescein dilaurate) for cholesterol ester hydrolase, esterase, secreted from the pancreas is orally administered and the urinary excretion or the blood level of the degradation product fluorescein is determined;

3. Fecal chymotrypsin test wherein chymotrypsin in the feces is quantitatively determined; and 4. Fecal elastase test wherein elastase in the feces is quantitatively determined.

However, the sensitivity of any of these tests is too low to detect slight decreases in pancreatic exocrine function.

Furthermore, the PFD and PLT tests require a long time to carry out and therefore cannot often be performed on outpatients and are not suitable in physical examinations or the like.

To solve these problems, a number of simpler pancreatic exocrine function tests have been reviewed. $^{13}$C-breath tests have also been applied wherein a $^{13}$C-labeled compound is administered and an increase in the concentration of $^{13}CO_2$ in the breath is determined. The following tests may be listed:

1. $^{13}$C-breath test wherein a $^{13}$C-labeled lipid or mixed triglyceride, which is a substrate for lipase, is administered (Chen et al., J. Nuclear Med., 15:1125 (1974); Watkins et al., J. Lab. Clin. Med., 90:422 (1977); Ghoos et al., Digestion, 22:239 (1981); John, S G., Gastroenterology, 83:44 (1982); Watkins et al., Gastroenterology, 82:911 (1982); Benini et al., Digestion, 29:91 (1984); Jones et al., J. Lab. Clin. Med., 105:647 (1985); Knoblach et al., Monatsschr Kinderheilkd, 136:26 (1988); Vantrappen et al., Gastroenterology, 96:1126 (1989); Murphy et al., Arch. Disease in Childhood, 65:574 (1990); Kato et al., Am. J. Gastroenterol., 88:64 (1993); McClean et al., Arch. Disease in Childhood, 69:366 (1993); Jakobs et al., Eur. J. Pediatr., 156:S78 (1997); and Kalivianakis et al., Eur. J. Clin. Invest., 27:434 (1997));

2. $^{13}$C-breath test wherein a $^{13}$C-labeled cholesterol ester, which is a substrate for cholesterol esterase, lipase, is administered (Mundlos, et al., Pediatric Res., 22:257 (1987); Cole et al., Gastroenterology, 93:1372 (1987); and Mundlos et al., Gut, 31:1324 (1990));

3. $^{13}$C-breath test wherein a $^{13}$C-labeled starch, which is a substrate for amylase, is administered (Hiele et al., Gastroenterology, 96:503 (1989); Dewit et al., Pediatric Res., 32:45 (1992); and Z. Gastroenterol., 35:187 (1997));

4. $^{13}$C-breath test wherein a $^{13}$C-enriched egg protein, which is a protein having the $^{13}$C-concentration increased from the natural abundance of 1.1 atm % up to 1.4 atm % by feeding a chicken with $^{13}$C-leucine and which is a substrate for protease, is administered (Y. Ghoos, $^{13}CO_2$-Breath Tests at the laboratory "Digestion-Absorption", University Hospital Gasthuisberg, Leuven, Belgium (1996)); and 5. breath test wherein a $^{13}$C-labeled peptide (Japanese Unexamined Patent Application Publication No. 2000-053697), a $^{13}$C-labeled fluorescein ester compound (Japanese Unexamined Patent Application Publication No. 2000-159773) or a $^{13}$C-labeled oligosaccharide or a cyclodextrin/$^{13}$C-labeled compound clathrate inclusion complex (Japanese Unexamined Patent Application Publication No. 2000-159810) is administered.

However, the methods 1 to 4 are also low in sensitivity and time-consuming. Therefore, these methods have not been established in clinical fields. In the method 5, the $^{13}$C-labeled compounds currently used in the test are expensive.

Under these situations, development of a simple pancreatic exocrine function test that imparts low stress on a subject, is less costly and gives accurate results in a short time has been demanded.

Thus, it is an object of the present invention to provide a diagnostic preparation for the diagnosis of pancreatic exocrine function which allows a simple, highly sensitive pancreatic exocrine function test that imparts low stress on a subject, is less costly and gives accurate results in a short time.

It is another object of the present invention to provide a new drug delivery system and enteric preparation.

DISCLOSURE OF THE INVENTION

The present inventors have found that using a preparation comprising a compound carried by a carrier composed of a substrate for a pancreatic exocrine enzyme, one can estimate pancreatic exocrine function by utilizing the phenomenon that the carrier is degraded when exposed to the action of the pancreatic exocrine enzyme so that the release rate of the compound from the carrier is enhanced. Thus, the present invention was completed.

Thus, the present invention provides a preparation for the diagnosis of pancreatic exocrine function by determining the amount in which a substance administered to a subject or a degradation product or metabolite thereof migrates into the blood and/or is excreted out of the body, wherein the substance is carried by a carrier and released from the carrier when exposed to the action of a pancreatic exocrine function-related factor.

The present invention also provides a drug delivery system comprising a medical agent carried by a carrier, wherein the medical agent is released from the carrier when exposed to the action of a pancreatic protease. In the drug delivery system, the target of the medical agent can be the superior part of the small intestine.

The present invention further provides a preparation comprising a medical agent carried by a carrier, wherein the medical agent is released from the carrier when exposed to the action of a pancreatic protease. The preparation can be used as an enteric preparation.

As used herein, the term "carrier" refers to any material that serves to retain and/or stabilize a substance administered to a subject or patient (e.g., a variety of elements and compounds) in a preparation and/or serves to deliver the substance to a desired part in the living body. Examples of the carrier include polymeric support media such as solidified egg white, lipids, polysaccharides, starch gels and albumin; particulate preparations such as tablets, capsules, powder and granules; and bio-derived substances such as erythrocytes and lipoproteins.

As used herein, the term "carry" means "to keep carrying". The manner in which a substance is carried by a carrier includes the following: the substance is dispersed and/or encapsulated in the carrier; the substance is adsorbed on the carrier; the substance is bound to the carrier; and so on.

As used herein, the term "disperse" or "dispersion" means that a substance is present as fine particles in a medium that is different from the substance. The fine particles can have variable particle sizes, and may be present as coarse particles (1 μm or greater), colloidal particles (1 μm to 1 nm) or molecules (10 nm or smaller). The manner in which a substance is dispersed in a carrier includes the following; the substance is contained in a matrix formed by the carrier (e.g., a polymeric matrix); molecules or particles of the substance are present within or between molecules of a material constituting the carrier; molecules or particles of the substance are present in the space(s) formed by one or more molecules of a material constituting the carrier; and so on.

As used herein, the term "encapsulate" or "encapsulation" means "to contain a substance and enclose it". The manner of encapsulation includes the following: a substance is encapsulated in microcapsules; a substance is covered with an outer coating; a protein contains a metal ion; and so on.

As used herein, the term "adsorb" or "adsorption" means that a substance is enriched or concentrated at the interface between two phases. An exemplary manner of adsorption is such that a substance is concentrated on the surface of a matrix formed by other substance (e.g., a polymeric matrix) via an ionic bond or the like.

As used herein, the term "bind" or "binding" means a concept including any type of binding of a substance to a carrier via a covalent bond (e.g., an ester bond). As an example, albumin-ethyl ester fine particles may be mentioned in which ethanol is bound to carboxyl groups in the protein via an ester bond. The substance to be bound to albumin may be any compound as long as it can bind to a carboxyl or hydroxyl group in albumin via an ester bond and if it is harmless and can be quantitatively determined in its free form. Examples of the compound include alcohols that are non-toxic to humans, such as ethanol; organic acids such as formic acid, acetic acid, propionic acid, pyruvic acid and benzoic acid; saccharides such as glucose; and amino acids such as alanine.

As used herein, the term a "pancreatic exocrine function-related factor" refers to a substance or environmental factor that is involved in or contributes to the pancreatic exocrine function, including, e.g., pancreatic exocrine enzymes (e.g., protease, lipase, amylase), pH of the intestinal juice, bicarbonate ion, sodium ion, chlorine ion, calcium ion and the amount or volume of the intestinal juice.

As used herein, the term a "medical agent" refers to any one of a variety of elements and compounds used for medicinal purposes.

As used herein, the term "enteric" refers to a property of being dissolved/disintegrated only after reaching the intestine without being dissolved/disintegrated in the stomach, or a property of being dissolved/disintegrated by low degree in the stomach but being dissolved/disintegrated by an increased degree in the intestine.

Hereinafter, the present invention will be described in detail.

The diagnostic preparation for pancreatic exocrine function of the present invention is a preparation for the diagnosis of pancreatic exocrine function by determining the amount in which a substance administered to a subject or a degradation product or metabolite thereof migrates into the blood and/or is excreted out of the body. The substance to be administered to a subject (hereinafter, also referred to as "administered substance") is carried by a carrier, e.g., in such a way that the substance is dispersed and/or encapsulated in the carrier, is adsorbed on the carrier, or is bound to the carrier. The carrier releases the carried substance under the action of a pancreatic exocrine function-related factor. In one embodiment of the present invention, the carrier experiences changes in its structure (e.g., decomposition or dissolution of the material constituting the carrier, change in the structure or intermolecular distance of the material constituting the carrier) or changes in the nature of its surface under the action of a pancreatic exocrine function-related factor, whereupon the substance carried on the carrier is released.

For example, the diagnostic preparation for pancreatic exocrine function of the present invention comprises a substance carried by a carrier composed of a material that can be degraded with a pancreatic exocrine enzyme or can be dissolved at pH of the intestinal juice which is increased due to the secretion of bicarbonate ions from the pancreas. Suppose this diagnostic preparation is orally administered to a subject; if the pancreatic exocrine function of the subject is low, the rate of degradation or dissolution of the carrier is also low and the release rate of the substance carried by the carrier is reduced. The substance released from the carrier is absorbed through the intestine, migrates into the blood, and then excreted either as such or in the form of its degradation product or metabolite into the urine or breath. The diagnosis for a decrease of pancreatic exocrine function can be made by comparing the amount of the released substance or the degradation product or metabolite thereof in the blood, urine or breath at predetermined time points after the administration or by comparing the time course of that amount.

The carrier is preferably composed of a material (substrate) that can be degraded with a pancreatic exocrine enzyme (e.g., protease, lipase, amylase) or a material that can be dissolved at pH of the intestinal juice (e.g., pH 4.5 to 8.5). The material used as a substrate may be properly selected depending on the type of the pancreatic exocrine enzyme to be tested.

The material that can be degraded with a protease may be any one that contains an amide bond or a peptide bond. Specific examples include proteins (e.g., egg white, gelatin, poly-L-lysine, albumin), peptides, polypeptides, cross-linked peptides and proteoglycans. The material that can be degraded with lipase may be any one that contains an ester bond, such as triglycerides and diglycerides. Specific examples include lipids (e.g., glycerin mono-fatty acid esters, glycerin di-fatty acid esters). Among them, glycerin monocaprylate, glycerin monostearate and polyethylene glycol monostearate are preferred. The material that can be degraded with amylase may be any one that contains an α-1,4-glycoside bond. Specific Examples include polysaccharides (e.g., starch, amylose, amylopectin, dextrin) and cross-linked oligosaccharides.

The material that can be dissolved at pH of the intestinal juice may be any compound that is commonly used in enteric preparations. Specific examples include cellulose acetate phthalate, carboxymethylethyl cellulose, hydroxypropylmethyl cellulose phthalate, hydroxypropylmethyl cellulose acetate succinate, methacrylate copolymer L, methacrylate copolymer LD, methacrylate copolymer S and shellac.

The aforementioned materials may be used alone or in combination as a mixture of two or more of them. The materials are not limited to those specifically mentioned above.

The administered substance may be any compound or element. The type of the substance is not limited, as long as the amount in which the substance or a degradation product or metabolite thereof migrates into the blood or is excreted out of the body (e.g., the amount of excretion in the urine or breath) can be determined.

In the case of determining the amount of migration into the blood, the administered substance or a degradation product or metabolite thereof is preferably such that it can migrate rapidly into the blood through the lumen of the digestive tract. The administered substance or a degradation product or metabolite thereof is also preferably such that it can be directly determined in the whole blood, serum or plasma, either as such or after pretreatment (e.g., deconjugation) or isolation/purification procedures, by a colorimetric, fluorometric, electrochemical or radiochemical/nuclear chemical method or the like. Even if the administered substance or a degradation product or metabolite thereof cannot be determined directly, they may be rendered indirectly quantifiable by converting them, either enzymatically or by means of a color reagent, an oxidation-reduction reagent or the like, into a substance that can be determined by a colorimetric, fluorometric or electrochemical method or the like.

Specifically, the substance which, either in the form of the administered substance or as a degradation product or metabolite thereof, can be directly determined by a colorimetric method includes, but is not limited to, indocyanine green, bromo sulphalein, neutral red, phenolsulfonephthalein and indigo carmine which all have a chromophore. The substance which can be determined directly by a fluorometric method includes, but is not limited to, fluorescent substances such as fluorescein, calcein and rhodamine. The substance which can be determined directly by an electrochemical method includes, but is not limited to, oxidation-reduction substances such as ferrocenecarboxylic acid, ascorbic acid, lithium ion and glutathione. The substance which can be determined directly by a radiochemical/nuclear chemical method includes, but is not limited to, compounds labeled with a radioisotope or stable isotope. The substance that can be determined indirectly by a colorimetric method includes, but is not limited to, p-aminobenzoic acid, 4-aminoantipyrine, sodium iodide, caffeine, xylose, alcohols (e.g., ethanol), organic acids (e.g., formic acid, acetic acid, propionic acid, pyruvic acid, benzoic acid) and saccharides (e.g., glucose). The substance that can be determined indirectly by a fluorometric method includes, but is not limited to, fluorescein diacetate. The substance that can be determined indirectly by an electrochemical method includes, but is not limited to, galactose, D-amino acids and glycolic acid.

In the case of determining the amount of excretion in the urine, the administered substance or a degradation product or metabolite thereof is preferably such that it can be excreted rapidly into the urine. The administrated substance or a degradation product or metabolite thereof is also preferably such that it can be directly determined in the urine, either as such or after pretreatment (e.g., deconjugation) or isolation/purification procedures, by a colorimetric, fluorometric, electrochemical or radiochemical/nuclear chemical method or the like. Even if the administered substance or a degradation product or metabolite thereof cannot be determined directly, they may be rendered indirectly quantifiable by converting them, enzymatically or by means of a color reagent, an oxidation-reduction reagent or the like, into a substance that can be determined by a colorimetric, fluorometric or electrochemical method or the like.

Specifically, the substance which, either in the form of the administered substance or as a degradation product or metabolite thereof can be directly determined by a colorimetric method includes, but is not limited to, phenolsulfonephthalein and indigo carmine which all have a chromophore. The substance which can be determined directly by a fluorometric method includes, but is not limited to, fluorescent substances such as fluorescein, calcein and rhodamine. The substance which can be determined directly by an electrochemical method includes, but is not limited to, oxidation-reduction substances such as ferrocenecarboxylic acid, ascorbic acid and lithium ion. The substance which can be determined directly by a radiochemical/nuclear chemical method includes, but is not limited to, compounds labeled with a radioisotope or stable isotope. The substance which can be determined indirectly by a colorimetric method includes, but is not limited to, p-aminobenzoic acid, 4-aminoantipyrine, sodium iodide, caffeine, xylose, alcohols (e.g., ethanol), organic acids (e.g., formic acid, acetic acid, propionic acid, pyruvic acid and benzoic acid, and saccharides (e.g., glucose). The substance which can be determined indirectly by a fluorometric method includes, but is not limited to, fluorescein diacetate. The substance which can be determined indirectly by an electrochemical method includes, but is not limited to, galactose, D-amino acids and glycolic acid.

In the case of determining the amount of excretion in the breath, the administered substance or a degradation product or metabolite thereof is preferably such that it is volatile or can be rapidly degraded or metabolized into $CO_2$ or ammonia. The administered substance or a degradation product or metabolite thereof is also preferably such that it can be directly determined in the breath, either as such or after pretreatment (e.g., trapping, concentration) or isolation/purification (e.g., trapping, concentration) or isolation/purification procedures, by a colorimetric, fluorometric, electrochemical or radiochemical/nuclear chemical method or the like. Even if the administered substance or a degradation product or metabolite thereof cannot be determined directly, they may be rendered indirectly quantifiable by converting them, either enzymatically or by means of a color reagent, an oxidation-reduction reagent or the like, into a substance that can be determined by a colorimetric, fluorometric or electrochemical method or the like.

The substance which, either in the form of the administered substance or as a degradation product or metabolite thereof, can be directly determined by a radiochemical/nuclear chemical method includes, but is not limited to, compounds labeled with a radioactive isotope (e.g., $^{14}C$) or a stable isotope (e.g., $^{13}C$, $^{15}N$). Specifically, the substance includes, but is not limited to, organic acids such as $^{13}C$-labeled $NaHCO_3$, $^{13}C$-labeled formic acid, $^{13}C$-labeled acetic acid, $^{13}C$-labeled propionic acid, $^{13}C$-labeled lactic acid, $^{13}C$-labeled butyric acid, $^{13}C$-labeled pyruvic acid and $^{13}C$-labeled benzoic acid; $^{13}C$-labeled amino acids such as $^{13}C$-labeled alanine; $^{13}C$-labeled saccharides such as $^{13}C$-labeled glucose; and $^{13}C$-labeled alcohols such as $^{13}C$-labeled ethanol.

The diagnostic preparation for pancreatic exocrine function of the present invention is preferably formulated into an oral dosage form (e.g., tablet, capsule, powder, granule, liquid) that can be delivered to the intestine without being affected in the stomach. Preferably, the diagnostic preparation is in the form of a liquid preparation having microcapsules or microspheres dispersed or emulsified in water. As the pharmaceutical additives for the formulation of the preparation, various excipients, aids and additives known in the art can be used. For example, the excipient includes saccharides (e.g., lactose, sucrose, glucose, mannitol), starches (e.g., potato starch, wheat starch, corn starch), inorganic compounds (e.g., calcium carbonate, calcium sulfate, sodium hydrogen carbonate, sodium chloride), crystalline cellulose, plant powder (e.g., licorice powder, gentian powder) and the like. The binder includes starch paste, gum arabic, gelatin, sodium alginate, methyl cellulose, ethyl cellulose, polyvinyl pyrrolidone, polyvinyl alcohol, hydroxypropyl cellulose, carmellose and the like. The disintegrant includes starch, agar, gelatin powder, crystalline cellulose, sodium carboxymethyl cellulose, calcium carboxymethyl cellulose, calcium carbonate, sodium hydrogen carbonate, sodium alginate and the like. The lubricant includes magnesium stearate, talc, hydrogenated plant oils, macrogol, silicone oils and the like. The suspending agent includes gum arabic, sodium alginate, methyl cellulose, sodium carboxymethyl cellulose, polyvinyl pyrrolidone, polysorbate 80, gum tragacanth, aluminum monostearate and the like. The emulsifying agent includes gum arabic, cholesterol, polyoxyl 40 stearate, sorbitan sesquioleate, polysorbate 80, sodium lauryl sulfate and the like. In addition, purified water and surfactants may also be used.

In one embodiment of the dosage form of the diagnostic preparation for pancreatic exocrine function of the present invention, a preparation in which a substance to be administered is carried by a polymeric matrix is provided. As the material forming the polymeric matrix, any material may be selected such that the structure of the matrix is changed under the action of a pancreatic exocrine function-related factor so that the substance can be released from the matrix. Such material includes, e.g., those substances which can be degraded with any one of the aforementioned pancreatic exocrine enzymes and those substances which can be dissolved at pH of the intestinal juice. The preparation in which the substance to be administered is carried by the polymeric matrix may be further covered with an enteric coating.

In another embodiment, a preparation in which a core including the substance to be administered is covered with an outer coating is provided. As the material that forms the outer coating, any material may be selected such that the structure of the outer coating is changed under the action of a pancreatic exocrine function-related factor so that the substance can be released from the core. Such material includes, e.g., those substances which can be degraded with any one of the aforementioned pancreatic exocrine enzymes and those substances which can be dissolved at pH of the intestinal juice. Two or more kinds of the material may be used so as to form a laminated outer coating. The preparation in which the core including the substance to be administered is covered with the outer coating may be further covered with an enteric coating. The core may be a tablet, capsule or granule.

In the preparation in which the substance to be administered is carried by the polymeric matrix or the preparation in which the core including the substance to be administered is covered with the outer coating, the particle diameter is preferably 2 nm to 20 mm, preferably 1 μm to 8 mm, more preferably 1 μm to 500 μm. For the purpose of increasing the gastric emptying rate of the preparation, a substance having high specific gravity (e.g., gold), an alkali (e.g., sodium hydrogen carbonate) or a component that can enhance gastric emptying (e.g., metoclopramide) may be added to the preparation, or the surface of the preparation may be treated to render it hydrophilic.

The preparation in which the substance to be administered is carried by the polymeric matrix or the preparation in which the core including the substance to be administered is covered with the outer coating is preferably microencapsulated and suspended or emulsified in water. The processes for producing microencapsulated preparations are known in the art and described in, e.g., Patric V. Deasy, Microencapsulation and Related Drug Process, Marcel Dekker Inc., New York (1984); U.S. Pat. No. 4,061,254; U.S. Pat. No. 4,818,542; U.S. Pat. No. 5,019,400; U.S. Pat. No. 5,271,961; and Wakiyama et al., Chem. Pharm. Bull., 29, 3363–68 (1981).

Alternatively, the preparation in which the substance to be administered is carried by the polymeric matrix or the preparation in which the core including the substance to be administered is covered with the outer coating may be filled in a capsule. In this case, it is preferred that the capsule itself be enteric, or soluble in the intestine.

The amount in which the substance to be administered is contained in the preparation may vary depending on the type of the preparation. Generally, the content is 1 to 99% by weight, preferably 1 to 10% by weight.

The preparation described above can also be used as a delivery system for a medical agent that targets the superior part of the small intestine, or as an enteric preparation.

In the pancreatic exocrine function test using the diagnostic preparation for pancreatic exocrine function of the present invention, the diagnostic preparation for pancreatic exocrine function of the present invention is orally administered. The pancreatic exocrine function is then diagnosed either from the data of the integral of the amounts in which the administered substance or a degradation product or metabolite thereof migrated into the blood or were excreted out of the body (e.g., the excreted amount in the urine or breath) at predetermined time points after the administration or from the data of the time course (onset slope, change in slope, peak time, etc.) of those amounts during a predetermined time period after the administration.

The method for the measurement of the amount of the administered substance or the degradation product or metabolite thereof is properly selected depending on the nature or type of the material to be tested (e.g., blood, urine, breath) and the substance to be administered. Examples of the method include colorimetry, fluorometry, mass spectrometry, NMR (nuclear magnetic resonance), HPLC, gas chromatography, gas chromatography-mass spectrometry (GC-MS), photoelectric acoustic spectroscopy, GM counter method, liquid scintillation, solid scintillation, autoradiography, and ionization chamber method.

Specifically, for determining the amount of migration into the blood, the collected blood may be measured directly, or the blood that is preliminarily subjected to some treatment (e.g., isolation, pretreatment) may be measured. For example, determination can be carried out by administering a diagnostic preparation containing a fluorescent compound to a subject, collecting the blood from the subject at predetermined time points after the administration, preparing serum or plasma from the blood, and then comparing the fluorescence intensity in the serum or plasma. In the case where a diagnostic preparation containing a pigment is administered, the blood is collected from the subject at predetermined time points after the administration and the concentration of the pigment in serum or plasma is then determined with a spectrophotometer or the like. Alternatively, the amount of the pigment in the blood may be determined externally on the skin of the subject without collecting the blood.

In the case where the urine is used as a sample, determination can be made by colorimetry, fluorometry, mass spectrometry, NMR (nuclear magnetic resonance), HPLC, gas chromatography or the like. The urine may be measured directly, or the urine that is preliminarily subjected to some treatment (e.g., isolation, pretreatment) may be measured. For example, determination can be carried out by administering a diagnostic preparation containing a fluorescent compound to a subject, collecting the urine from the subject at predetermined time points after the administration, and then comparing the fluorescence intensity in the urine. In the case where a diagnostic preparation containing a pigment is administered, the urine is collected from the subject at predetermined time points after the administration and the concentration of the pigment in the urine is then determined with a spectrophotometer or the like.

For determining the amount of excretion in the breath using, e.g., a diagnostic preparation containing a $^{13}$C-labeled compound, determination can be carried out by gas chromatography-mass spectrometry (GC-MS), infrared spectroscopy, mass spectroscopy, photoelectric acoustic spectroscopy, NMR (nuclear magnetic resonance) or the like on $^{13}CO_2$. In the case where a diagnostic preparation containing a $^{14}$C-labeled compound is used, the breath, either directly or after trapping $CO_2$ in a solvent, can be subjected to measurement with a GM counter, a liquid scintillation counter or a solid scintillation counter or by autoradiography, ionization chamber method or the like.

Prior to the administration of the diagnostic preparation for pancreatic exocrine function of the present invention to a subject, a test meal or the like may be given to the subject to stimulate the secretion of pancreatic exocrine enzymes. Alternatively, the diagnostic preparation may be administered together with a test meal.

The substance to be administered must be contained in the diagnostic preparation for pancreatic exocrine function of the present invention in sufficient amount to enable determining or confirming the increase of the substance to be detected (e.g., the substance administered or a degradation product or metabolite thereof) in the sample after administration. It will be varied depending on the age and body weight of a subject and the intended purpose of the test. For example, the unit dose may be about 1 to 2,000 mg/kg of body weight for an adult.

The drug delivery system and the enteric preparation provided by the present invention enables delivering a medical agent in such a way that it can be absorbed through the digestive tract including and downstream of the duodenum. Accordingly, they are useful for the delivery of a medical agent which presents inconvenience if degraded with gastric acid or an enzyme in the stomach or which may cause a disorder if absorbed through the stomach. Examples of the medical agent include iron agents (e.g., ferric pyrophosphate, soluble), bifidus preparations, laxatives for constipation (e.g., bisacodyl, sennoside) and aspirin.

Since the drug delivery system and enteric preparation provided by the present invention have a property of delivering a medical agent in such a way that it can be absorbed through the digestive tract including and downstream of the duodenum, they can provide controlled release of a medical agent. Therefore, by utilizing its delayed release, the medical agent can be prevented from causing any adverse side effects while sustaining its beneficial effects. Examples of the medical agent include cephem antibiotics (e.g., pindolol, cephalexin), chlorpheniramine maleate, griseofulvin and etretinate.

The present application claims priority to Japanese Patent Application No. 2000-272116, the disclosure and/or the drawings of which are incorporated herein by reference.

BEST MODE FOR CARRYING OUT THE INVENTION

Hereinbelow, the present invention is illustrated in more detail by the following examples, however the scope of the present invention shall not be limited by the examples.

EXAMPLE 1

Solidified egg white containing trypan blue was immersed in a buffer with or without trypsin, and the time course of trypan blue elution was compared.

1-1: Method

A small amount of trypan blue was added to egg white and dissolved therein by fully stirring while preventing the formation of foam. The egg white colored in dark blue was put in a dialyzing tube (diameter: 5 mm, MWCO: 12–14,000), and boiled in a 0.4% trypan blue solution until it solidified. After 7 or 8 minutes, the dialyzing membrane was cut and removed to give two pieces of cylinder-shaped solidified egg white (5 mm in diameter×25 mm in length).

One piece of the solidified egg white was immersed in (i) 15 mL of 200 mM Pipes-K (pH 7.0), and the other was immersed in (ii) 15 mL of 200 mM Pipes-K (pH 7.0) containing 0.1% trypsin.

An aliquot (200 µl) was sampled from each of the solutions over time, and the amount of eluted trypan blue was determined by measuring the absorbance at 590 nm with a microplate reader (Molecular Device).

1-2: Results

Figure 1:
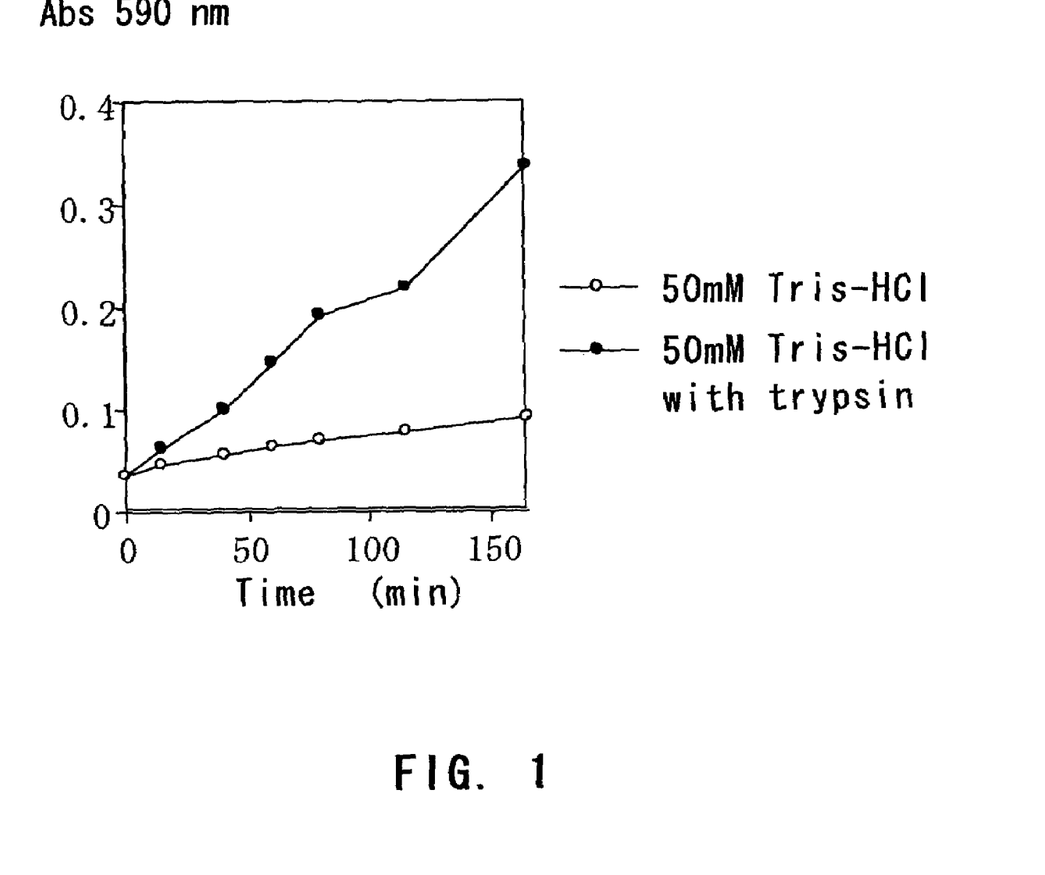
FIG. 1 shows the time course plot of the amount of trypan blue (absorbance at 590 nm) eluted from trypan blue-containing solidified egg white.

At 40 minutes after the immersion was initiated, the absorbance at 590 nm was 0.056 in (i) 5 mL of 50 mM Tris-HCl (pH 8.0) and 0.099 in (ii) the buffer with trypsin. Thus, the elution of trypan blue was enhanced over the blank by the addition of trypsin (FIG. 1). At 165 minutes after the immersion was initiated, the absorbance at 590 nm was 0.092 in (i) 5 mL of 50 mM Tris-HCl (pH 8.0) and 0.338 in (ii) the same buffer with trypsin. Thus, a significant difference was observed.

EXAMPLE 2

A starch gel containing trypan blue was immersed in each of a buffer with the duodenal juice, a buffer with amylase and a buffer, and the time course of trypan blue elution was compared.

2-1: Method

A hydrolyzed starch for electrophoresis (Wako) was added to a 0.16% trypan blue solution (0.35% NaCl) to give a final concentration of 10% and then heated while stirring. When the mixed solution was viscous and clear, the solution was aspirated with a disposable measuring pipette (diameter: 4 mm) while preventing the formation of foam and solidified in cold water. After cooling for 1 hour, the gelated starch was pushed out of the measuring pipette, thereby giving three cylinder-shaped starch gels (4 mm in diameter×10 mm in length).

The gels were immersed in (i) 5 mL of 50 mM Tris-HCl (pH 8.0), (ii) 5 mL of 50 mM Tris-HCl (pH 8.0) plus 1 mL of a 344 U/L amylase solution and (iii) 5 mL of 50 mM Tris-HCl (pH 8.0) plus 1 mL of the duodenal juice (the duodenal extract solution), respectively.

An aliquot (200 µl) was sampled from each of the solutions over time, and the amount of eluted trypan blue was monitored by measuring the absorbance at 590 nm with a microplate reader (Molecular Device).

The duodenal juice was prepared by removing the duodenum from an 8-week old male Wistar rat fasted overnight, incising the duodenum, adding the incised duodenum to 1 mL of 50 mM Tris-HCl (pH 8.0), agitating the mixture with a vortex mixer and then removing tissues.

2-2: Results

Figure 2:
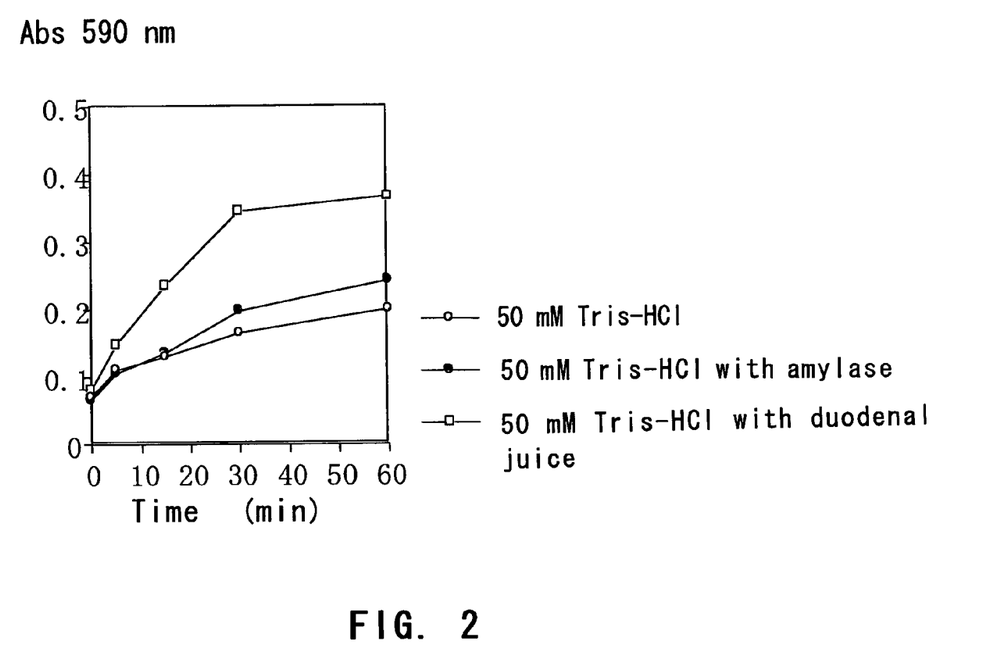
FIG. 2 shows the time course plot of the amount of trypan blue (absorbance at 590 nm) eluted from trypan blue-containing starch gel.

At 30 minutes after the immersion was initiated, the absorbance at 590 nm was 0.165 in (i) 5 mL of 50 mM Tris-HCl (pH 8.0), 0.198 in (ii) the buffer with amylase, and 0.346 in (iii) the buffer with the duodenal juice. Thus, the elution of trypan blue was enhanced over the blank by the addition of amylase and the duodenal juice (FIG. 2).

EXAMPLE 3

Solidified egg white containing $^{13}C$—$NaHCO_3$ and fluorescein was administered intraduodenally to a rat with chronic pancreatitis and a control rat under anesthesia. The time course of the $^{13}CO_2$ concentration in exhaled $CO_2$ and the fluorescein concentrations in the blood and urine were compared.

3-1: Method 40 mg of $^{13}C$—$NaHCO_3$ (Mastorace) and 3.2 mg of fluorescein were dissolved in 1 mL of distilled water, and then 7 mL of egg white was added. The resulting solution was mixed gently by pipetting while preventing the formation of foam. The mixed solution was poured into a chamber slide (Nunc, Cat# 177453), heated at 80° C. for 15 minutes to solidify the egg white containing $^{13}C$—$NaHCO_3$ and fluorescein. After being left to cool, the solidified egg white was cut out with a disposable measuring pipette (4 mm in diameter), thereby forming a cylinder of solidified egg white (200 µL in volume).

The chronic pancreatitis rat was prepared by injecting oleic acid into the pancreatic duct of a 5-week old male Wistar rat and then keeping the rat for 3 weeks in accordance with the method of Mundlos et al. (Mundlos et al., Pancreas 1:29 (1986)). As a control, a rat that had been subjected to only midline incision was used.

After fasting overnight, the chronic pancreatitis rat and the control rat, both 8 week-old, were fixed supinely under anesthesia. The breath was collected at a rate of about 100 to 300 ml/min using a stroke pump (Variable Stroke Pump VS-500, Shibata Kagaku Kogyo) and introduced directly to the flow cell of a $^{13}CO_2$ analyzer EX-130S (Nihon Bunko). A Perma Pure drier (MD-050-12P, Perma Pure INC.) was placed between the rat holder and the stroke pump to remove water vapor from the breath. When the $CO_2$ concentration stabilized, 200 µL of the solidified egg white containing $^{13}C$—$NaHCO_3$ and fluorescein was administered intraduodenally to the rat. The $CO_2$ concentration in the collected breath was held at 3±0.5%.

Output data from the $^{13}CO_2$ analyzer were AD converted and input to a personal computer (Apple Power Macintosh 8500). Using a data processing software package Lab VIEW (National Instruments), 10 pieces of data were integrated and averaged every 100 msec at intervals of 5 seconds and converted to $^{13}C$ atom %, $\Delta^{13}C$ (‰) and $CO_2$ concentration (%). In this manner, the $^{13}C$-breath test was continuously carried out. The converted data were displayed real time and stored in a hard disc.

$\Delta^{13}C$ (‰) was calculated from the $^{13}C$ concentration in the exhaled $CO_2$ at each time point ($^{13}C_{tmin}$) and the $^{13}C$ concentration in standard $CO_2$ ($^{13}C_{std}$) according to the following equation:

$$\Delta^{13}C(‰)=[(^{13}C_{tmin}-^{13}C_{0min})/^{13}C_{std}]\times 1000$$

After performing the breath test for 20 minutes, the blood and urine were collected. To the collected blood was added a 3.8% sodium citrate solution at a volume one-sixth of the blood, and the resulting solution was centrifuged at 10,000 g for 20 minutes to give a plasma as the supernatant.

The amount of fluorescein in the plasma was determined following the description in the Journal of Osaka Medical University 52(2):27–35. 50 µL of the plasma was added with 400 µL of a 0.5N KOH solution in ethanol, and the mixed solution was heated at 70° C. for 1 hour and then cooled. To the resulting solution was added 800 µL of 0.15M $MgSO_4$, and the solution was centrifuged at 10,000 g for 5 minutes. The amount of fluorescein in the supernatant was determined with a fluorescence microplate reader (Molecular Device) (excitation wavelength: 485 nm, fluorescence wavelength: 538 nm, sample load amount: 200 µL/well). The amount of fluorescein in an untreated plasma was also determined with a fluorescence microplate reader (Molecular Device).

The amount of fluorescein in the urine was determined following the method described in Archives of Disease in Childhood (1986) 61:573. 50 µL of the urine was added with 450 µL of 0.1N NaOH, and the resulting solution was heated at 70° C. for 10 minutes. The amount of fluorescein was measured with a fluorescence microplate reader (Molecular Device) (excitation wavelength: 485 nm, fluorescence wavelength: 538 nm, sample load amount: 200 µL/well).

3-2: Results

The degree of increase of $\Delta^{13}C$ (‰) starting 5 minutes after the administration onward was calculated according to the following equation:

$$\text{Degree of increase of } \Delta^{13}C(‰) = \Delta^{13}C(‰)_{nmin} - \Delta^{13}C(‰)_{5min}$$

Figure 3:
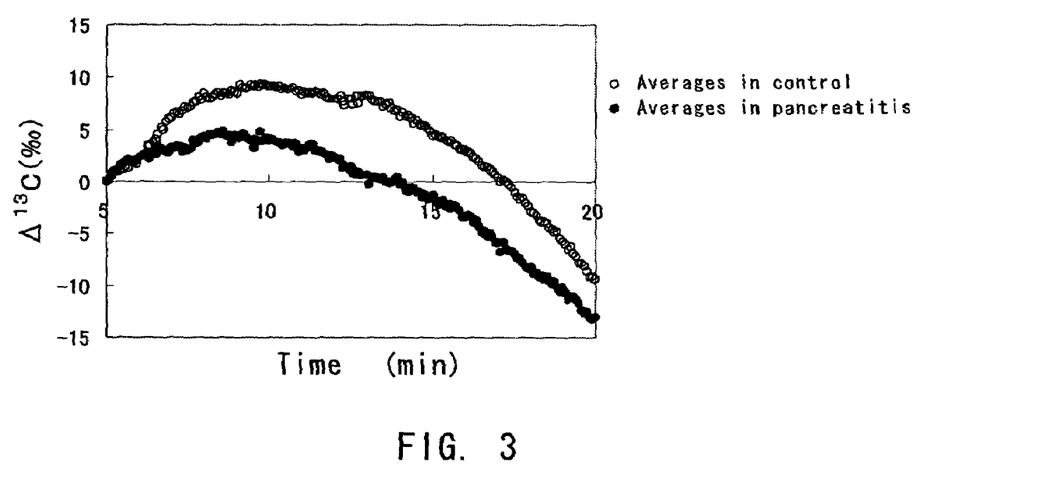
FIG. 3 shows the time course plot of the degree of increase of $\Delta^{13}C(‰)$ starting five minutes after the administration of $^{13}C$—$NaHCO_3$— containing solidified white egg onward.

The comparison of the time course revealed that the degree of increase of $\Delta^{13}C$ (‰) starting 5 minutes after the administration onward in the chronic pancreatitis rat was smaller than that in the control rat (FIG. 3). The degree of increase of $\Delta^{13}C$ (‰) at 10 minutes after the administration was 9.1‰ in the control rats (n=3) and decreased to 3.9‰ in the chronic pancreatitis rats (n=3). The degree of increase of $\Delta^{13}C$ (‰) at 20 minutes after the administration was −9.5‰ in the control rats and decreased to −13‰ in the chronic pancreatitis rats.

The fluorescein concentration (fluorescence intensity) in the deconjugated plasma at 20 minutes after the administration was 2.16 RFU in the chronic pancreatitis rats (n=3), which was lower than the value of 2.69 RFU in the control rats (n=3). The fluorescein concentration (fluorescence intensity) in the untreated plasma was 20.18 RFU in the chronic pancreatitis rats (n=3), which was lower than the value of 29.43 RFU in the control rats (n=3). The fluorescein concentration (fluorescence intensity) in the urine at 20 minutes after the administration was 1.53 RFU in the chronic pancreatitis rats (n=3), which was again lower than the value of 4.05 RFU in the control rats (n=3).

The results demonstrate that the diagnosis of the decrease in pancreatic exocrine function can be achieved by administering $^{13}C$—$NaHCO_3$ and fluorescein contained in an egg white carrier.

EXAMPLE 4

A starch gel containing [1-$^{13}C$]alanine and fluorescein was administered intraduodenally to chronic pancreatitis rats and control rats under anesthesia. The time course of the $^{13}CO_2$ concentration in exhaled $CO_2$ and the concentrations of fluorescein in the blood and urine after the administration were compared.

4-1: Method 0.5 g of a hydrolyzed starch for electrophoresis (Wako), 40 mg of [1-$^{13}C$]alanine (Masstrace) and 3 mg of fluorescein were added to 5 mL of 50 mM borate buffer (pH 8.5), and the solution was stirred while heating by boiling in hot water. When the solution became viscous and clear, about 300 µL of the solution was aspirated with an insulin injecting syringe with a cut tip (Terumo, for 0.5 mL injection) while preventing the formation of foam, and then left to cool to cause gelation. The syringe was cut so that the volume of the gelated starch contained in the syringe was 150 µL.

Thereafter, the same procedure as in Example 3 was performed.

4-2: Results

Figure 4:
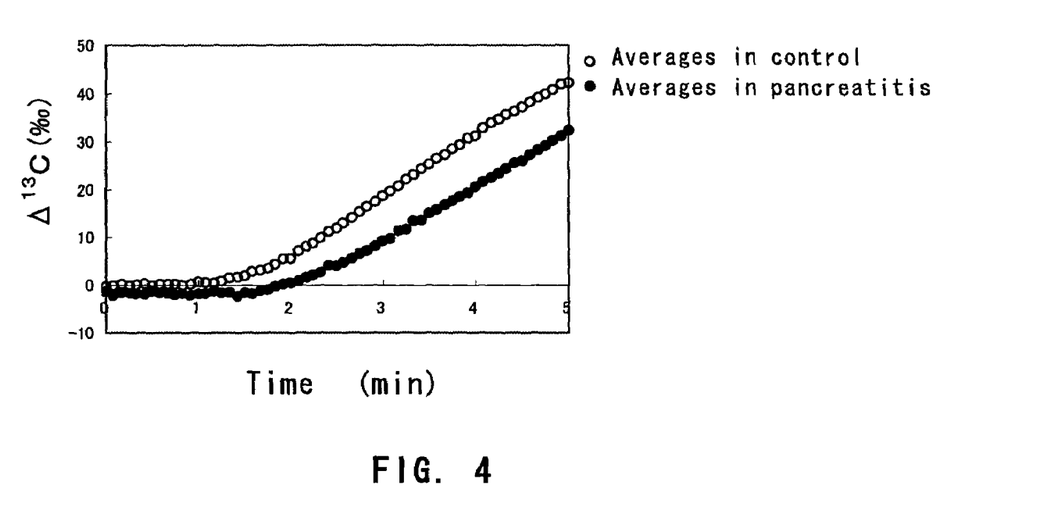
FIG. 4 shows the time course plot of $\Delta^{13}C(‰)$ after the administration of [1-$^{13}$C]alanine-containing starch gel.

The values of $\Delta^{13}C$ (‰) in the chronic pancreatitis rats were smaller than those in the control rats (FIG. 4). $\Delta^{13}C$ (‰) at 5 minutes after the administration was 42.2‰ in the control rats (n=3) and decreased to 32.2‰ in the chronic pancreatitis rats (n=2).

The fluorescein concentration (fluorescence intensity) in the plasma at 20 minutes after the administration was 6.67 RFU in the chronic pancreatitis rat (n=1), which was lower than the value of 9.33 RFU in the control rats (n=3). The fluorescein concentration (fluorescence intensity) in the urine at 20 minutes after the administration was 4.14 RFU in the chronic pancreatitis rats (n=2), which was obviously lower than the value of 60.50 RFU in the control rats (n=2).

The results demonstrate that the diagnosis of the decrease in pancreatic exocrine function can be achieved by administering [1-$^{13}C$]alanine and fluorescein contained in a starch gel carrier.

EXAMPLE 5

Fine particles of albumin-ethyl ester were prepared, added to the duodenal juice from a normal rat and a chronic pancreatitis rat, and the time course of the concentration of ethanol released from the fine particles was compared.

5-1: Method 26 mL of thionyl chloride (Wako) was slowly added dropwise to 100 mL of ethanol (Wako) that had been cooled to 0° C. in an argon atmosphere. The solution was stirred for 10 minutes and then warmed to room temperature. To the solution now at room temperature, 6.64 g of human serum albumin was added and the mixture was stirred for 24 hours. The reaction solution was filtered, and the residue was dried with nitrogen gas, thereby giving 7.6453 g of albumin-ethyl ester.

Fine particles of the albumin-ethyl ester were prepared following the method of Gallo et al. (1984) (International Journal of Pharmaceutics Vol.22 (1984) pp.63–74). 0.5 mL of 13.3% albumin-ethyl ester was added to 30 mL of olive oil, and the resulting solution was subjected to sonication (125 W) for 2 minutes while cooling in ice. The solution was transferred to a 50 mL syringe and added dropwise to 100 mL of olive oil that had been heated to 125° C. at a rate of 1 to 2 drops/sec. After stirring at 1,500 rpm for 10 minutes, the solution was allowed to stand for 1.5 hours and then cooled to room temperature. After adding 60 mL of ether and stirring, the solution was centrifuged at 3,000 g for 15 minutes. The resulting precipitate was added with 25 mL of ether, suspended by sonication, and then centrifuged at 3,000 g for 15 minutes. After repeating the same procedure once again, the resulting precipitate was resuspended in 10 mL of ether and allowed to stand in a draft at room temperature to remove the ether.

To 25 μL of the resulting suspension of albumin-ethyl ester fine particles (10 mg/mL in D.W.) were added 50 μL of a solution of 150 U/mL of alcohol dehydrogenase (Sigma) in 360 mM phosphate buffer (pH 7.8), 100 μL of a color reagent (38 mM NAD, 1.0 mM nitrotetrazolium blue, 0.1 mM 1-methoxy PMS, 88 mM sodium acetate) and 5 μL of the duodenal juice. The solution was allowed to react in a microplate at 37° C. As a blank, a reaction was performed by adding distilled water in place of the duodenal juice. The amount of released ethanol was monitored by measuring the absorbance at 560 nm over time with a microplate reader (Molecular Device).

The duodenal juice was prepared by removing the duodenum from each of a normal rat and a chronic pancreatitis rat, incising the duodenum, immersing the incised duodenum in 2 mL of 50 mM carbonate buffer, and then centrifuging the solution at 10,000 g for 15 minutes.

5-2: Results

Figure 5:
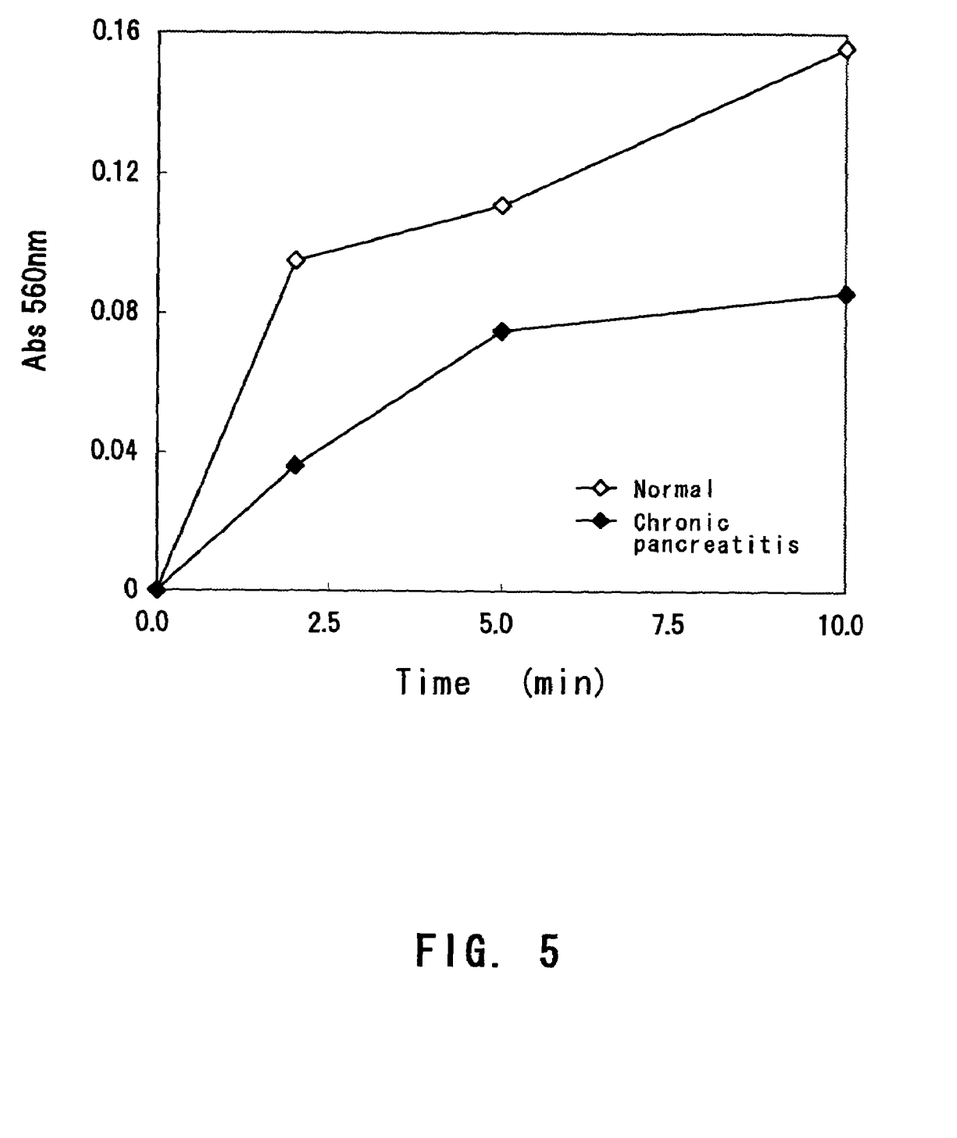
FIG. 5 shows the time course plot of the amount of ethanol (absorbance at 560 nm) released from albumin-ethyl ester fine particles.

At 2 minutes after the duodenal juice was added, the release of ethanol into the sample containing the duodenal juice from the normal rat was enhanced compared with the sample containing the duodenal juice from the chronic pancreatitis rat (FIG. 5). At 10 minutes after the duodenal juice was added, the absorbance at 560 nm was 0.156 in the sample with the duodenal juice from the normal rat and 0.086 in the sample with the duodenal juice from the chronic pancreatitis rat. Thus, a difference was observed.

All publications, patents and patent applications mentioned in this specification are herein incorporated by reference.

Applicability of the Invention

The preparation for the diagnosis of pancreatic exocrine function of the present invention allows a simple pancreatic exocrine function test that imparts low stress on a subject, is less costly and gives accurate results in a short time. The test method can be used in pancreatitis screening in mass physical examination or total health check, determination of the severity of chronic pancreatitis, prediction of the possibility toward aggravation of fulminating pancreatitis of which mortality is still high (30%), diagnosis of the etiology of pancreatitis, and early diagnosis of pancreatic cancer. The test method is also useful as a diagnostic method for denial of the possibility of pancreatitis in the diagnosis of general outpatients.

The preparation can also be used as a drug delivery system which targets the superior part of the small intestine and as an enteric preparation.

What is claimed is:

1. A method for diagnosis of pancreatic exocrine function, comprising:
   administering to a subject a carrier containing a $^{13}$C-labeled substance, said carrier being a substrate for a pancreatic exocrine enzyme and containing an amide bond, a peptide bond, or a α-1, 4-glycoside bond, said $^{13}$C-labeled substance being released from the carrier when exposed to an action of the pancreatic exocrine function enzyme; and
   determining an amount of the substance administered to a subject or a degradation product or metabolite of the substance that migrated into the blood and/or is excreted out of the body of the subject to ascertain a level of the pancreatic exocrine function of the subject.

2. The method of claim 1, wherein a radiochemical/nuclear chemical method is implemented to determine the amount of the substance administered to a subject or a degradation product or metabolite of the substance that migrated into the blood and/or is excreted out of the body of the subject.

3. The method of claim 1, wherein the amount of the substance or a degradation product or metabolite of the substance is determined from the blood, urine, or breath of the subject.

4. A method for diagnosis of pancreatic exocrine function, comprising:
   administering to a subject a carrier containing a $^{13}$C-labeled substance, said carrier being a substrate for a protease or an amylase, said $^{13}$C-labeled substance being released from the carrier when exposed to an action of the protease or the amylase; and
   determining an amount of the substance administered to a subject or a degradation product or metabolite of the substance that migrated into the blood and/or is excreted out of the body of the subject, to ascertain a level of the pancreatic exocrine function of the subject.

5. The method according to claim 1, wherein the $^{13}$C-labeled substance comprises $^{13}$C-labeled organic acids, amino acids, saccharides or alchohols.

6. The method according to claim 1, wherein the $^{13}$C-labeled substance comprises: $^{13}$C-labeled NaHCO$_3$, $^{13}$C-labeled formic acid, $^{13}$C-labeled acetic acid, $^{13}$C-labeled propionic acid, $^{13}$C-labeled lactic acid, $^{13}$C-labeled butyric acid, $^{13}$C-labeled pyruvic acid or $^{13}$C-labeled benzoic acid.

7. The method according to claim 1, wherein the $^{13}$C-labeled substance comprises: $^{13}$C-labeled alanine.

8. The method according to claim 1, wherein the $^{13}$C-labeled substance comprises: $^{13}$C-labeled glucose.

9. The method according to claim 1, wherein the $^{13}$C-labeled substance comprises: $^{13}$C-labeled ethanol.

10. The method according to claim 1, wherein the carrier comprises: polymeric support media.

11. The method according to claim 1, wherein the carrier comprises: solidified egg white, polysaccharides, starch gels, or albumin.

12. The method according to claim 1, wherein the carrier comprises lipoproteins.

13. The method according to claim 1, wherein the carrier contains a $^{13}$C-labeled substance dispersed or encapsulated therein, or adsorbed thereon.

* * * * *